United States Patent [19]
Dempster et al.

[11] 4,271,701
[45] Jun. 9, 1981

[54] GAS FLOW MEASURING SYSTEM

[75] Inventors: Philip T. Dempster; John Y. Pun, both of St. Helena, Calif.

[73] Assignee: Cavitron Corporation, New York, N.Y.

[21] Appl. No.: 886,741

[22] Filed: Mar. 15, 1978

[51] Int. Cl.$^3$ .............................................. G01F 1/38
[52] U.S. Cl. ................................. 73/861.42; 73/717; 128/725
[58] Field of Search ................. 73/205 R, 205 L, 702, 73/717; 128/2.07, 2.08, DIG. 29, 725

[56] References Cited

U.S. PATENT DOCUMENTS

| | | | |
|---|---|---|---|
| 3,195,028 | 7/1965 | Werner et al. | 73/718 X |
| 3,295,370 | 1/1967 | Marx | 73/231 R |
| 3,296,868 | 1/1967 | Koppel et al. | 73/205 R X |
| 3,509,767 | 7/1968 | Greer . | |
| 3,924,612 | 12/1975 | Dempster et al. | 128/2.08 |

*Primary Examiner*—James J. Gill
*Attorney, Agent, or Firm*—Robert M. Skolnik; William R. Evans

[57] ABSTRACT

The pressure difference across a pneumotach restriction is sampled with a gas chopper connected across a pressure difference detecting transducer. The gas chopper alternates the pressures backward and forward in application to the transducer so that the latter develops an AC sampling signal, the strength of which is related to flow. This AC signal is sampled in synchronism over intervals having a duration related to the power line frequency to develop an integrated value of the pressure difference free of drift caused by power line interference. The resultant signal is smoothed and summed in alternating response at double the gas chopper sampling rate to give a smooth output which is then multiplied by a linearizing circuit to obtain a flow signal which is proportional to the pressure difference. Specific gas flow structures and electronic sampling circuitry are disclosed.

11 Claims, 7 Drawing Figures

GAS FLOW MEASURING SYSTEM

BACKGROUND OF THE INVENTION

This invention relates generally to gas flow measuring systems and more particularly to pulmonary measurement devices known as spirometers. More particularly, the invention relates to gas flow measuring systems of the open end flow type in which the flow in a channel is caused to pass a restriction in order to develop a pressure difference across the restriction in proportion to flow in the channel. Devices of this type in spirometers are known as pneumotachs. Once a pressure difference has been established, it is possible to measure and integrate the pressure difference to obtain values of flow rate and total volume through the channel or pneumotach.

Reference is made to U.S. Pat. No. 3,924,612 entitled *SPIROMETER APPARATUS AND METHOD* issued Dec. 9, 1975 to Philip T. Dempster and John Y. Pun. As therein disclosed, a rotary air pressure chopper was employed to pneumatically ground a pressure transducer measuring the pressure difference caused by the restriction in the pneumotach. The output pulses produced were measured against a reference level taken at atmospheric pressure. That system is in general a shunt type system in which the air chopper is synchronized with an electronic circuit which is driven to zero reference level during the atmospheric shunt referencing of the chopper and to develop a signal indicative of the pressure developed across the restriction in the pneumotach during the other portion of the cycle. Suitable electronic circuitry including a sample and hold circuit and buffer amplifiers were there provided for smoothing the sampled output and developing a continuous signal, the value of which is proportional to the flow through the pneumotach. The device disclosed in U.S. Pat. No. 3,924,612 works satisfactorily but possesses several limitations such as the need to use a small restriction and relatively large size smoothing chamber connected in series between the measuring transducer and the pneumotach. In practice, the restriction is subject to clogging, and the large size smoothing chamber required makes sensitive measurements of flow difficult. That system also had a continuous leak of gas from the system due to shunt operation and was not well suited for bi-directional flow measurement.

More specifically, there is a need for a gas flow measuring system which is particularly adapted for bi-directional flow measurement in a flow channel and which does not permit leakage from the channel. Bi-directional measurements are needed in applications, for example, where a patient is connected to a ventilator which is basically a pump for facilitating forced breathing of the patient. In such applications, measurement of the flow both during inhalation and exhalation is desired in a completely closed system and the flow measuring device should be capable of operating independently, i.e., without being affected by the pressure in the flow circuit. In many cases the flow being measured may be quite a bit smaller than the system pressure. In other applications of industrial consequence the pressure in the flow circuit may be relatively high and it may be highly desirable that zero leakage occur from the flow measuring system. There is, therefore, a need for a new and improved flow measuring system which will overcome the above limitations and disadvantages.

The present invention also finds particular application as a gas flow analyzer in carbon monoxide, carbon dioxide, nitrogen and oxygen flow measuring systems and in many other gas flow measuring systems in which a toxic or gaseous flow is to be measured and which must be maintained in isolation from atmosphere. Other applications include neonate, i.e. newborn baby monitoring especially for premature babies under treatment for hyaline membrane disease where a continuous pressure is applied to the patient together with a simulated respiratory pattern. In such systems, gas flow must be measured by systems also capable of ignoring the common mode line pressures as well as capable of bi-directional measurement.

The general method employed in the present invention utilizes classical techniques in which the flow is measured as the electrical output of a pressure transducer which is linearized as the pressure transducer senses the flow across a pneumotach restriction as will be set forth. Volume measurement is provided by time integration of the flow measurement.

As used herein, pneumotach means any device incorporated as part of a flow channel and having a restriction therein for developing a pressure difference on opposite sides A, B thereof in response to flow through said restriction and in said channel and is not restricted to medical diagnostic apparatus.

OBJECTS OF THE INVENTION

In general, it is an object of the present invention to provide a gas flow measuring system which will overcome the above limitations and disadvantages.

Another object of the invention is to provide a gas flow measuring system of the above character having unique closed loop system in which transducer is alternately referenced to the high and low pressure side across the flow restriction of the pneumotach and further in which the gas sampling mechanism is entirely contained within a smoothing chamber of the structure while the transducer housing is contained entirely within a second smoothing chamber within the structure.

Another object of the invention is to provide a gas flow measuring system of the above character which is located within a closed loop and therefore not subject to leakage.

Another object of the invention is to provide a gas flow measuring system of the above character which permits bi-directional measurement of gas flow independent of flow line pressure.

Another object of the invention is to provide a gas flow measuring system of the above character which is insensitive to baseline or reference drift.

Another object of the invention is to provide a gas flow measuring system of the above character which is predicated upon development of an AC measuring signal which is taken over an interval related to power line frequency such that drift normally caused by the power line is cancelled out.

Another object of the invention is to provide a gas flow measuring system of the above character in which the sampling period of the system is taken over a significant portion of the measurable signal and is integrated over that time.

Another object of the invention is to provide a gas flow measuring system which is particularly adapted for the measurement of extremely low gas flows as in the treatment of emphysemics and is further particularly adapted to measurement of such flows at extremely sensitive pressures as in the treatment of hyaline membrane disease in which a continuous pressure is applied through the gas flow system.

Another object of the invention is to provide a gas flow measuring system of the above character which is particularly adapted for the measurement of noxious gases and which is relatively insensitive to shock and vibration.

The foregoing objects have been achieved in the present invention by employing a restriction for creating a pressure difference in a pneumotach flow channel, each side of which is connected to opposite sides of a pressure transducer via a gas chopper which alternates the connection by means of a rotating shaft having bores therein which alternately connect suitable channels connected to the transducer to each respective side of the restriction. In this way the gas pressure is alternated back and forth at the transducer which thereby creates an alternating current electrical signal output, the magnitude of which is monotonically related to the flow through the flow line or pneumotach and phase dependent on direction of flow. This electrical output signal is amplified, sampled and linearized to develop a bi-directional DC signal in correspondence with the flow being measured. More specifically, the magnitude of the envelope of the AC signal is sampled at intervals about the peak excursions of the signal and is averaged in a predetermined sequence by sample and hold electronic circuitry to develop a smooth flow signal which is not referenced to a zero baseline of the device but which is referenced to itself. The sampling is done at a rate sufficiently high to avoid baseline drift and other DC drift problems associated with the chopper gas flow system and the transducer. Preferably a piezoelectric AC generated transducer is employed and is sampled over an interval corresponding to a cycle of the power line frequency, i.e., 16.7 milliseconds at 60 cycles, to cancel power line associated drift. During the sampling period means is provided for integrating the signal waveform for a significant period to obtain the maximum average signal information available.

A further object of the invention is to provide a gas flow measuring system of the above character in which a common mode pressure is nulled out and is not measured.

A further object of the invention is to provide a gas flow measuring system of the above character which is designed to utilize a piezoelectric type pressure transducer which has low susceptability to damage by shock and overpressure and also provides a good signal to noise ratio.

A further object of the invention is to provide a gas flow measuring system of the above character having two smoothing chambers, one of which completely contains the gas flow chopper and the other of which completely contains the transducer support and associated chambers whereby leakage within the same is self-contained.

These and other objects and features of the invention will become apparent from the following detailed description when taken in conjunction with the accompanying drawings of which:

DETAILED DESCRIPTION OF THE PREFERRED EMBODIMENT

Figure 1:
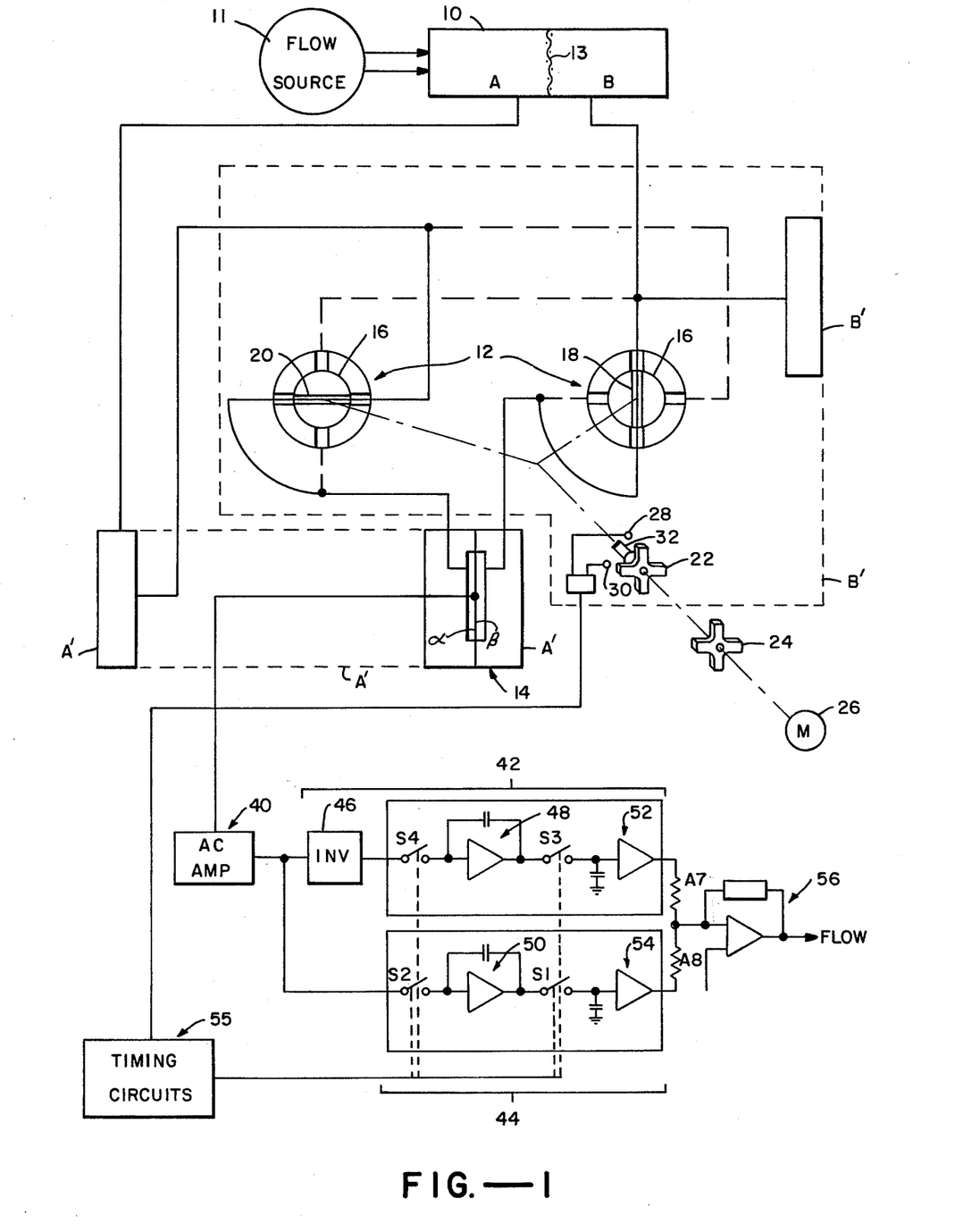
FIG. 1 is a schematic diagram of the gas flow measuring system of the present invention showing one connection state of the gas flow chopper thereof to the pneumotach.
Figure 2:
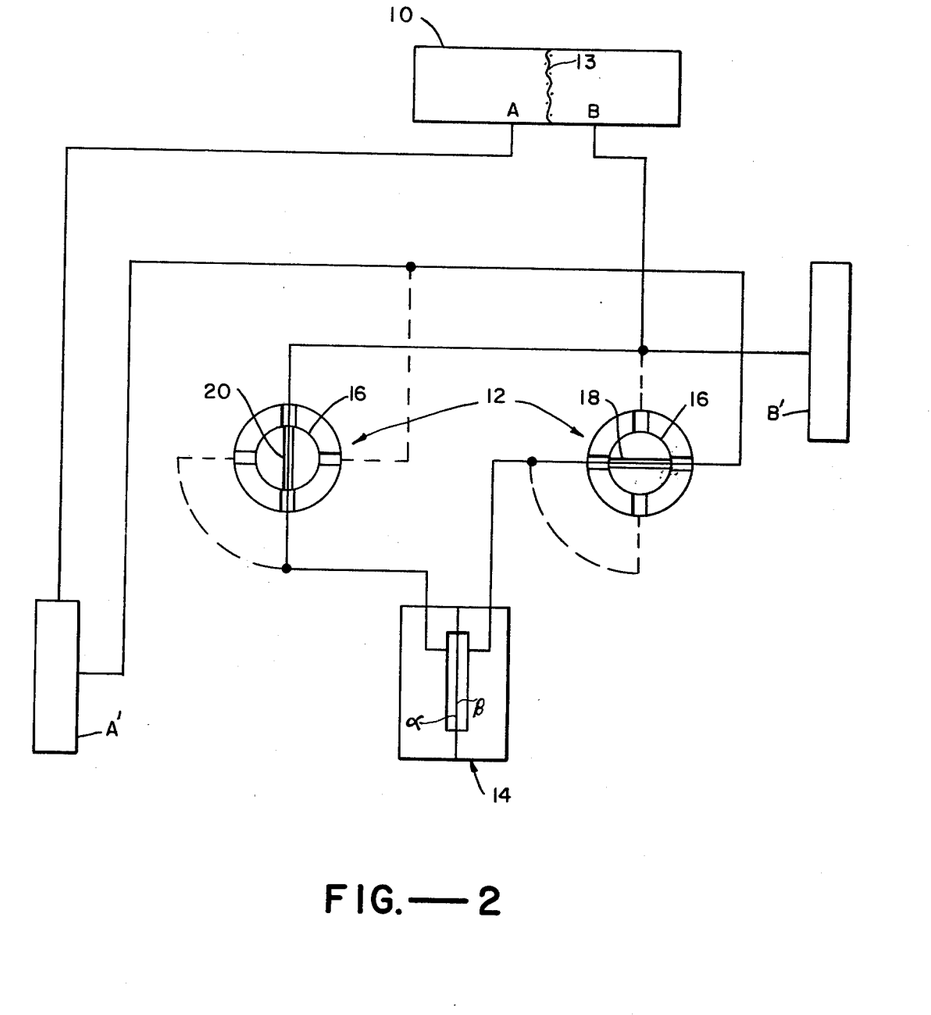
FIG. 2 is a partial schematic diagram similar to that shown in FIG. 1 showing the gas flow measuring system of the present invention with the gas flow chopper connected in the alternate state.

Referring now particularly to FIGS. 1 and 2 there is shown a gas flow measuring system of the present invention in schematic form and it includes a pneumotach 10 or other means defining a flow channel which is connected in series with a flow source such as a patient. Typically, the patient or other flow source 11 may be breathing into a pneumotach as part of a spirometer apparatus or may be connected to a ventilator passing through the pneumotach or flow restriction device contained in line with the patient. In industrial applications the flow source 11 may be any typical flow device in which a restriction may be placed to develop a pressure difference responsive to flow thereacross. The output at A and B on each side of the flow restriction is taken through suitable lines to smoothing chambers A' and B' and thence to the input sides of a flow chopper device indicated schematically at 12. As further shown schematically, the entire flow chopper is contained within smoothing chamber B'. A pressure transducer having a small gas chamber $\alpha,\beta$ on each side is located within a mounting block indicated at 14, the mounting block being entirely contained within the smoothing chamber A'. Connection between the gas flow chopper and transducer block is obtained by suitable channelling within the body of the gas chopper mechanism as is illustrated in FIGS. 3 and 4 and as will be further explained in detail.

In accordance with the present invention, the gas chopper is rotated continuously which causes alternating connection of the pressure appearing within the smoothing chambers A' and B' forward and backward across the chambers $\alpha$ and $\beta$ of the transducer block. This is accomplished by providing a shaft 16 having transverse bores 18, 20 therethrough connecting with channelling within the chopper connected in the equivalent manner to that shown in FIGS. 1 and 2, these figures illustrating the manner in which alternate connection of the pressure difference is obtained. The shaft of the chopper is driven by a magnetic wheel 22 connected at one end thereof within chamber B' which is driven by a second magnetic wheel 24 located outside of the device and connected to a suitable rotary output electric motor 26. Positioning detection of the orientation of the chopper shaft is obtained by a pair of photoelectric cells or photosensors 28, 30 interrupted by an indexing vane 32 mounted on the chopper shaft.

Further to FIG. 1, the electronic processing circuit of the present invention is shown in generally schematic form and comprises a transducer amplifier 40, the output of which is taken through two circuits 42, 44, one of which contains an inverter 46 for changing the sign of the output signal. Each signal channel is provided with a series pair of signal switches S1, S2 and S3, S4 respectively. S2, S4 connect and disconnect a respective one of integrators 48, 50 from the input signal appearing thereat, while the complementary set of switches S1, S3 follows the integrators and serves to connect and disconnect their output to sampling and hold circuits 52, 54. An electronic timing circuit 55 senses the rotary position of shaft 16 via vane 32 and controls switches S1, S2, S3, S4. The outputs of the sample and hold circuits are summed through resistors A7 and A8. The summation is caused to occur in a pattern in which each signal is used twice to give a satisfactorily smooth output signal which is in direct relation to the signal developed by the pressure transducer and to the difference in pressure appearing across a restriction 13 in the flow channel. This summed signal is further linearized to represent the actual flow in the channel by a scale factor adjusting circuit at 56.

Figure 3:
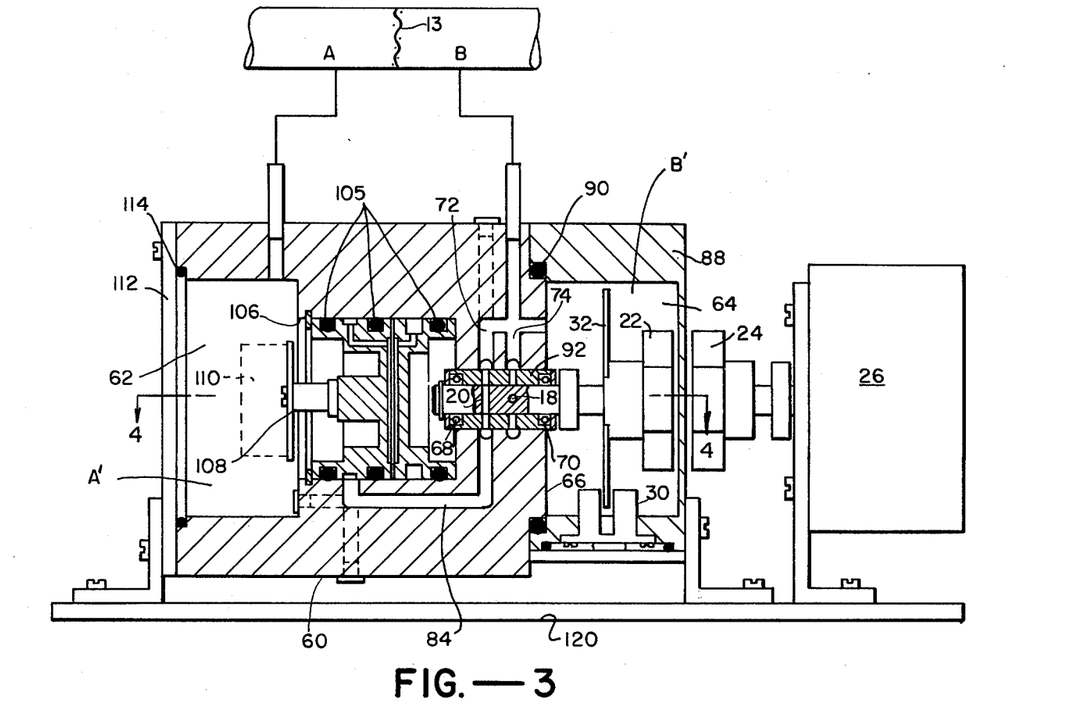
FIG. 3 is a cross-sectional elevation of the gas flow chopper of FIG. 1 showing a pneumotach connection thereto in schematic form.
Figure 4:
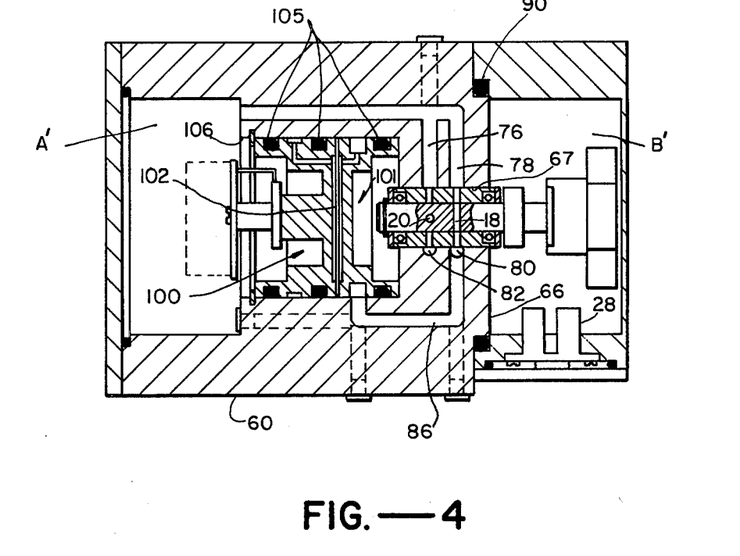
FIG. 4 is a transverse cross-sectional view of the gas chopper of FIGS. 1 and 3 taken along the lines 4—4 of FIG. 3.

Referring now more particularly to FIGS. 3 and 4, the detailed structural features of the gas chopper and transducer housing will now be discussed. Means is provided for forming a sealable enclosure for the chopper and for forming smoothing chambers A' and B' and can consist, for example, of a block 60 of Delrin (trademark), which is a solid machinable plastic, having defined openings 62, 64 at each end and an inner tranverse wall 66 dividing the same into two compartments A' and B'. The wall is penetrated by a bore 67 through which is set shaft 16 on precision sealed, ball bearings 68, 70 for supporting the same at each end in sealable relation to the wall 66. The shaft is drilled with transverse non-intersecting bores 18, 20 at right angles to each other and in axially spaced locations on the shaft. Upon rotation of the shaft these bores become aligned with fixed bores 72, 74 and 76, 78 formed in the Delrin block together with channels 80, 82 formed through the wall of the block to these fixed bores to connect to other channels 84, 86 and to the chambers A' and B', respectively. The gas connection provided by these bores and channels is shown diagramatically in FIGS. 1 and 2 and is shown structurally in FIGS. 3 and 4. It is shown particularly in FIGS. 3 and 4 that alignment of the shaft bore 20 vertically connects one side B of the pneumotach and chamber B' to side $\alpha$ of the transducer while simultaneously bore 18 is perpendicular and connects side A of the pneumotach and chamber A' to side $\beta$ of the transducer. As the shaft rotates, as shown in FIG. 2, the connection is reversed. Every 90° the cross connection is obtained through the arcuate channels 84, 86 partially encircling the bearing shaft housing. The structure of FIGS. 3 and 4 implements the foregoing and shows the connection of FIG. 2.

Means is provided for rotating the chopper shaft and consists of the electric motor 26 mounted externally of the chopper block and carrying on its output shaft a segmented magnetic pole rotor 24 which is magnetically coupled to a similar rotor 22 mounted on the end of the chopper shaft on opposite; inside of the chopper block housing wall. For convenience of manufacture, the wall is operable and resealable by forming the same as an end cap 88 and O-ring seal 90. The chopper shaft also has mounted thereon the position sensing vane 32 which interrupts the pair of photosensors 28, 30 mounted on the side walls in the chopper housing in chamber B'. The angular position of the vane is shown arbitrarily in the figures for clarity. Since the vane is keyed to the shaft chopper it allows use of the photosensors to recognize electronically which connection of the pneumotach sides A, B to the transducer chambers $\alpha$, $\beta$ by the shaft is operative at a given time. The photosensors can consist of an LED light source and phototransistor interrupted as the vane passes through a path intersecting the same. The gas chopper itself consists of a stainless steel chopper shaft set in a precision sleeve 92 and supported therein on the ball bearings 68, 70 at each end. The sleeve and shaft together with the bearings maintain a pneumatic seal between chamber B' and the remainder of the chopper structure.

Referring also to FIGS. 3 and 4, there is also shown the transducer mounting block 100, 101 which may, for example, be constructed of machined brass. The parts of the brass are joined together sandwiching an interposed transducer support disc 102 upon which the piezoelectric transducer is mounted. The support disc is made out of thin brass forming a diaphragm while the solid state substrate material, i.e., piezoelectric transducer is mounted thereon. The substrate thus may be taken at one polarity and forms one pole of the contact while the diaphragm itself forms the other side of the contact. The joined brass blocks 100, 101, interposed diaphragm 102, and piezoelectric transducer are then formed into a unitary structure as by cementing them and are provided with gas isolation grooves containing O-rings 105 for forming seals which closely fit against the inside wall of a cylindrical recess 106 formed within the Delrin block. The end of the transducer housing that extends towards chamber A is provided with a small heat sink 108 onto which is mounted a power transistor and thermal sensors, diagramatically indicated at 110, which cause the transistor to be heated adequately to maintain a constant temperature within the block. That end of the Delrin block on the outside at chamber A' is sealed by suitable end plate 112 and O-ring gasket 114 for convenience of manufacture and assembly. The entire unit is conveniently mounted on a suitable base plate 120. It should be particularly noted that the volume for the gas within the respective chambers A' and B' and associated passageways on the pneumotach side of the shaft is made equal so that the compressibility and other factors relating to these smoothing chambers is the same on each side of the system. In addition, the gas volumes associated with the small chambers on each side of the pressure transducer and the associated channels on that side of the gas chopping shaft are also constructed to be equal for the same reason. In the present construction the sleeve forming the chopper shaft is in a block of material so arranged as to provide a short pathway between the various parts for increased efficiency. Extremely short gas pathways are designed right into the chopper block itself by providing volume matched passageways between the smoothing chambers and volume matched passageways between the transducer chambers to provide highly identical volumes A', B'. Thus, every attempt is made to match the gas volumes on each side in the design and structure itself. In practice it was found that about 55 cubic centimeters was the minimum size volume required on each side for the flow lines (passageways) and the smoothing chambers and in order to provide adequate smoothing. If less than this amount is utilized a waveform deterioration can occur in the output signal of the transducer. It should be noted that changing gas flow between the lines causes no appreciable disturbance since there is minimal flow through the device itself, merely the alternating interconnection of the pressure available at each side of the pneumotach restriction. Therefore, measurement occurs by measuring only the pressure change within the particular dead spaces provided in the chopper housing.

Figure 5:
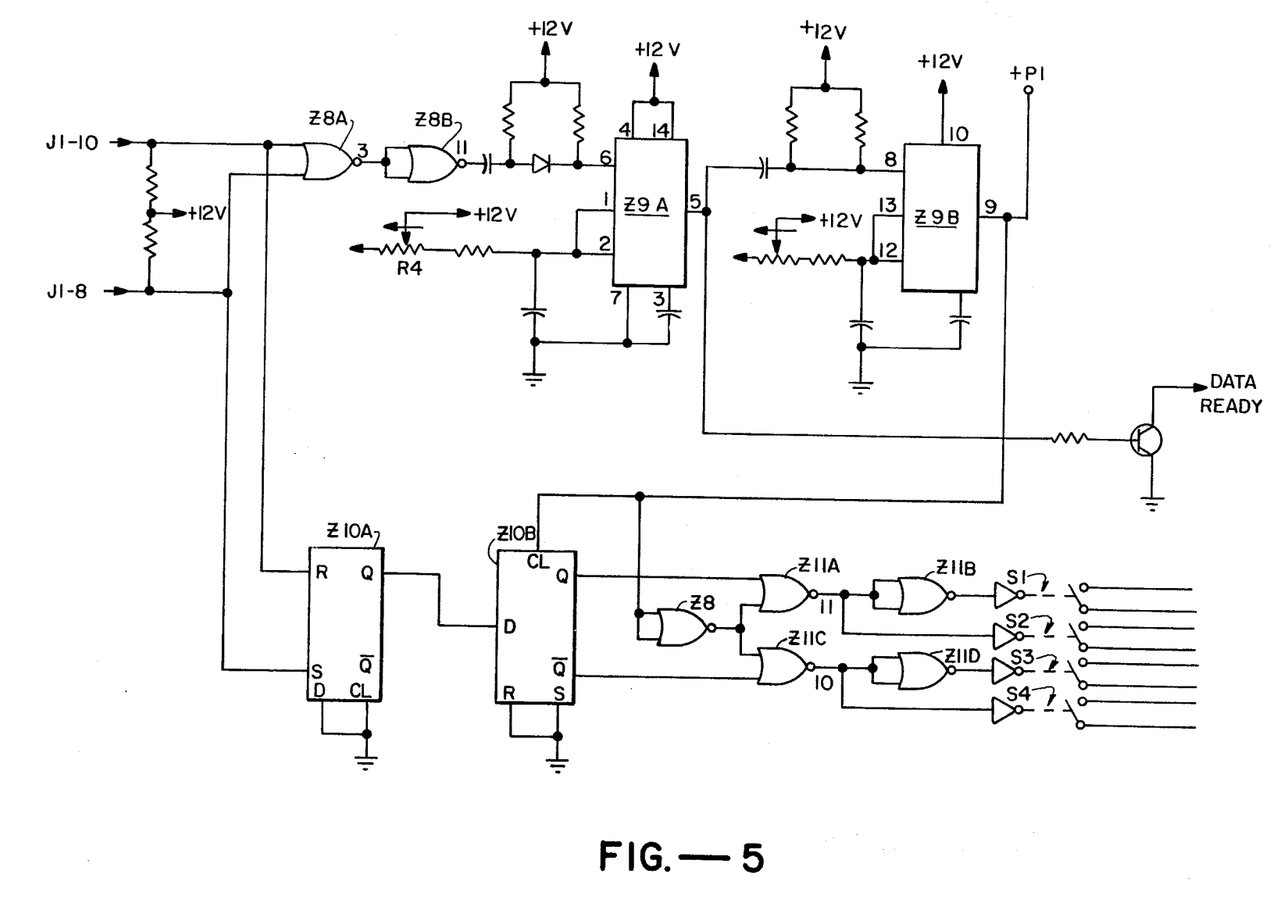
FIG. 5 is a detailed schematic diagram of the timing and switching circuit portion of the electronic circuits of FIG. 1 for sampling and processing the electrical transducer output in accordance with the present invention.
Figure 6:
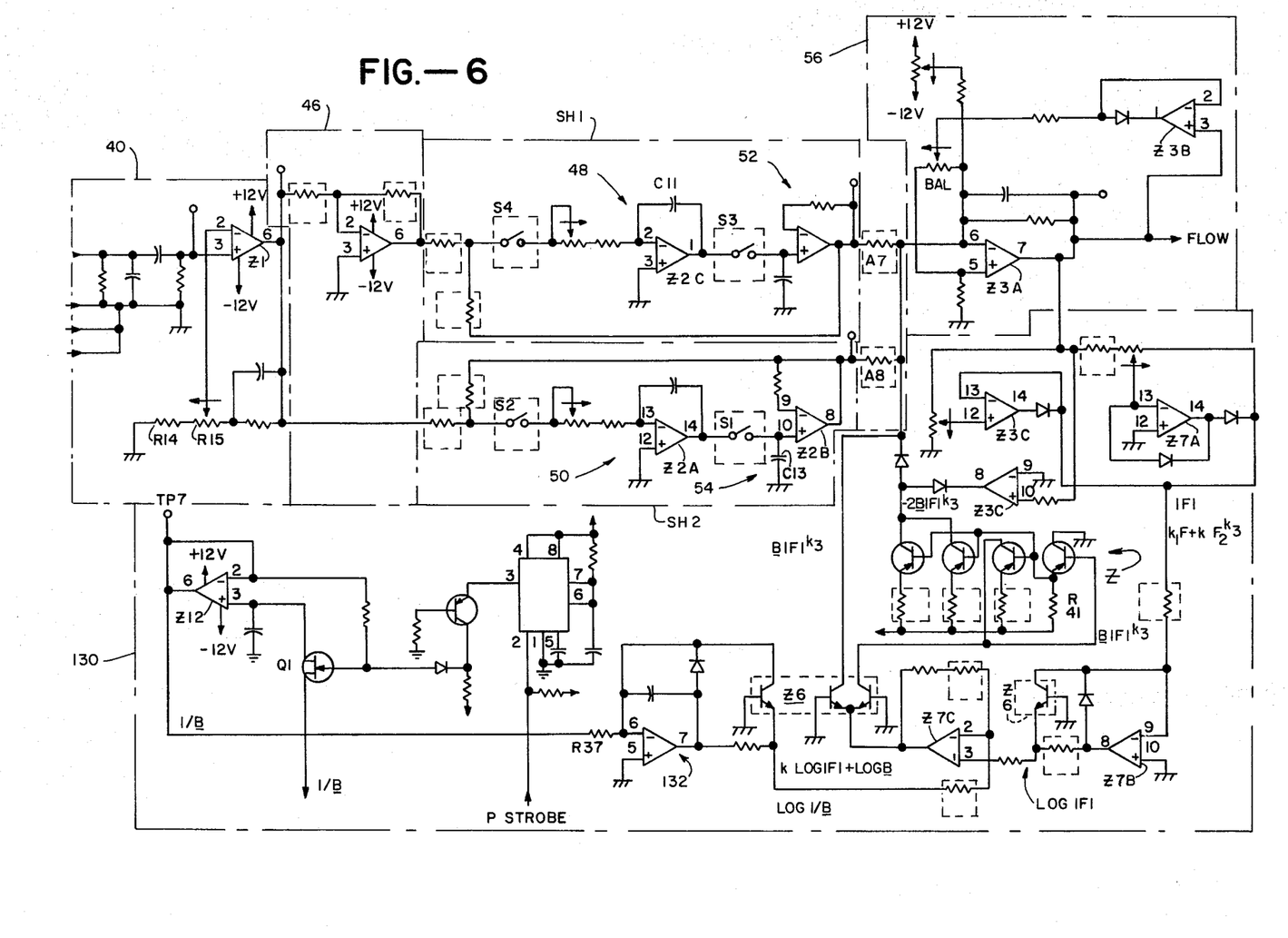
FIG. 6 is a detailed schematic diagram of the flow signal circuit portion of the electronic circuits of FIG. 1 for sampling and processing the electrical transducer output in accordance with the present invention.
Figure 7:
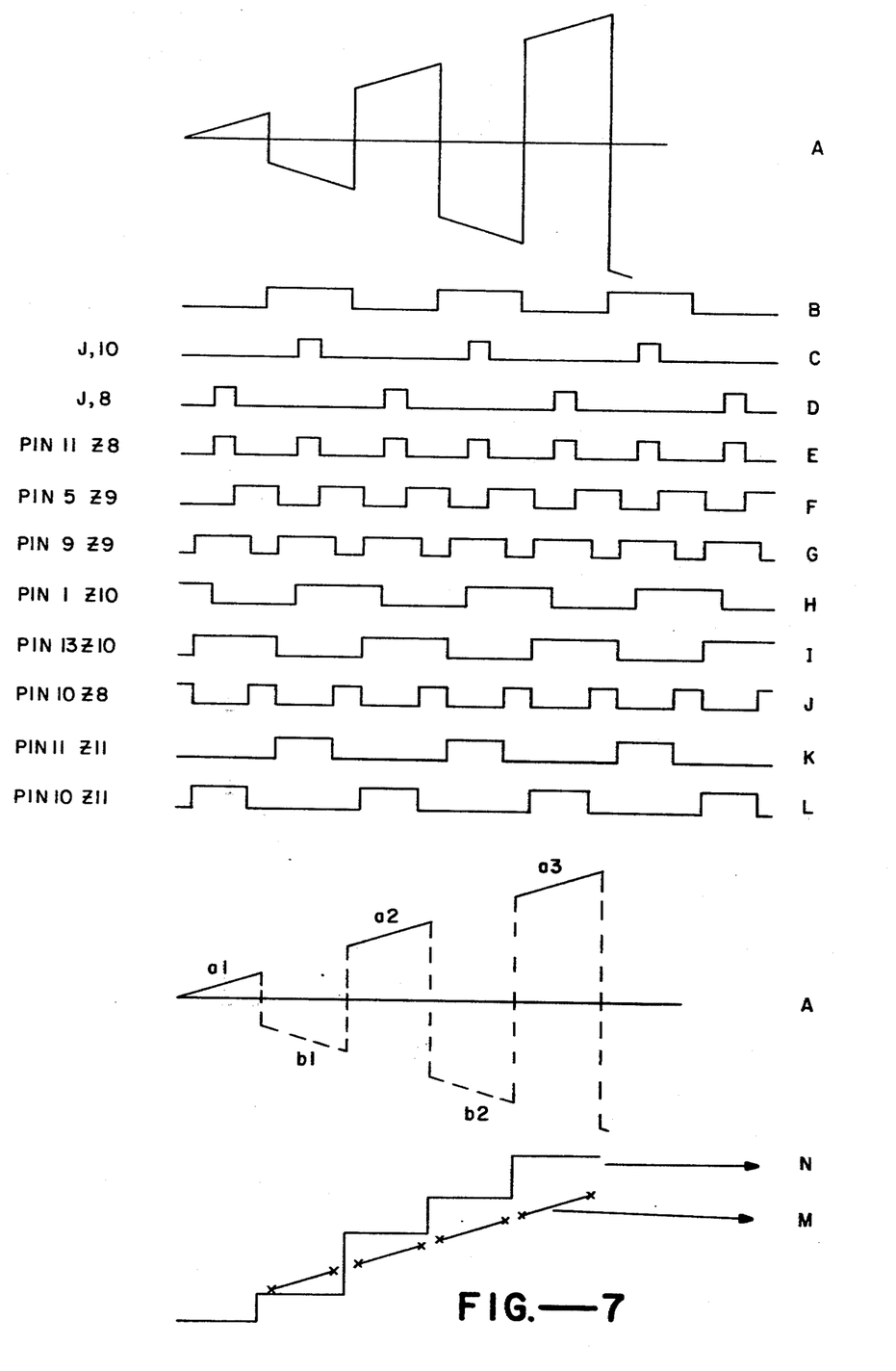
FIG. 7 is a series of waveforms A-N showing development of the output signal waveform and taken at various locations in the electronic circuitry of the present invention. The timing diagrams of the various circuits are self-explanatory from consideration of the desired circuit structures given.

Electronic Sampling and Analysis Circuitry (FIGS. 5 and 6)

Means is provided for amplifying the transducer signal and consists of an operational amplifier Z1 (3140) also having one input connected through an adjustable resistance R15/R14 to ground for serving as a gain control. The output of Z1 is taken through parallel integrating sample and hold circuits SH1 and SH2 to a summing junction of matched resistors A7 and A8. The sum is representative of the value of the pressure difference ($\Delta P$) and is converted to a flow output signal by being applied to the input of op amp Z3A which is arranged for operation as a non-linear amplifier by virtue of feedback loops containing op amps Z3B, Z3C, and Z7A, Z7B, Z7C, for forming the inverse function F from equation 1 below.

The transducer output at the junction of A7 and A8 is convertible to a direct measurement of the flow rate in the pneumotach flow channel in accordance with the following discussion. Flow is found to be related to the pressure drop through the pneumotach by the relation $$\Delta P = k_1(F + k_2 F^{k_3})  \quad (1)$$

where $\Delta P$ is the pressure difference and F is the flow rate under measurement. This function has been determined to be a good approximation due to the flow head characteristic for devices of the type shown and described herein. It is straightforward to form the inverse of this function by employing the foregoing equation as the solution to a feedback component in an operational amplifier circuit. The coefficients $k_1$ and $k_3$ are characteristic of the apparatus and can be fixed experimentally. $k_2$ is found to be proportional to atmospheric pressure over the range of flow measurement employed with spirometers and like flow instruments and is therefore arranged to be varied in response to barometric pressure and to be entered by the user.

Each sample and hold circuit consists of a first sample portion including an op amp Z2A and Z2C which integrates its input, i.e., the transducer output during the sampling period when S2 and S4 are closed, and which is connected by the latter switches and serves as a sample value hold circuit during the remainder of each cycle. One sample and hold circuit is preceded by unity gain inverting amplifier 46 to develop the signal minus b.

Since each switch pair S1, S2 and S3, S4 of the respective circuits are complementary, the outputs take values $a_n$, $b_n$, immediately following and for the entire period following each sample period until the next sampling pulse alternates the output. Thus, the value at the summing junction becomes $(a_1-b_1, a_2-b_1, a_2-b_2, a_3-b_2) \ldots (a_n-b_n), (a_{n+1}-b_n), (a_{n+1}-b_{n+1}), \ldots$ Derivation of the sample and hold timing signals will now be described. The output of the photosensors is delivered to the input of an adjustable timing circuit Z9A and Z9B. Z9A is an adjustable length one shot multivibrator triggered by either photosensor output signal drop which serves as an input to the sample one shot Z9B which is triggered by the falling edge of the Z9A output pulse. Z9A causes the latter to occur after the photodetector signal occurance to allow time for stabilization of the pneumatic circuit before sampling. Z9B is a one shot multivibrator having an adjustable output length to provide a 16.7 millisecond sample pulse.

A steering circuit is provided for blocking and unblocking the sample pulses and therefore for controlling the complementary switches S1, S2, S3, S4 of the sample and hold circuits. The steering circuit consists of an input photodetector output controlled set-reset flip flop Z10A which is set to one state or the other depending upon the last photodetector pulse received. The output of Z10A is connected to the data input of the D-flip flop which has one output Q for controlling one side of steering circuits Z11A, Z11B and the other output $\overline{Q}$ for controlling the other side of Z11C and Z11D.

The following discussion amplifies the foregoing and supplies additional details relating to the foregoing circuits.

The outputs of the photosensors 28, 30 result in signals that are synchronous to one or the other connection (pneumatic) of the chopper. These signals Z8A and Z8B are "or"ed in Z8 and pass into a one shot Z9A of variable length. This one shot serves basically to delay these pulses for one quarter revolution, the function adjusting resistor R4 of the one shot Z9A being to arrange for fine adjustment of the timing without changing the pneumatic/mechanical system directly since that is more difficult than adjusting the waveforms. The outputs of the two photosensors also go to a set-reset flip flop Z10A the output of which goes to the data input of a D-flip flop Z10B. The output of the one shot Z9A triggers (trailing edge) a second one shot Z9B which is set to have a timing period of 16.7 milliseconds corresponding to one cycle of a 60 hertz waveform. The rising portion of that waveform now sets the D-flip flop Z10B so that the output of that flip flop now is on or off depending upon which output is being looked at, i.e., depending on what the last position of the indexing vane was at the time that the basic timing circuit fired. The output of this circuit goes along with the output of the 16.7 millisecond flip flop and drives logic circuits Z10B and Z11A, Z11B, Z11C, Z11D which steers the 16.7 millisecond pulses to one set of switching circuits S1, S2, S3, DS4 or to the other.

Basically, the sampling circuits SH1 and SH2 consist of a conventional sample and hold circuit which, using SH2 as an example, consists of the operational amplifier Z2B to the right, the capacitor C13 and the switch S1. Feeding this sampling circuit is an integrator Z2A fed through switch S2 by the difference between the input and the output already held on the sampling circuit 52. This circuit is so set up so that if it is in adjustment, this difference is integrated during the 16.7 millisecond period in such a fashion that the integrator is sent aiming toward the new value from the last value held and transferred. If a constant input is assumed and suppose that this integrated output misses in that the integrator is too sensitive and the difference between the last value and the new value to be obtained is less than the device is about to indicate, i.e., the difference is integrated to a new value, it moves the integrator to a new position and it overshoots so that when S3 closes the output is too high. However, during the next sampling period there is no change in input—so that the too high value is fed back to the integrator. This error is now integrated by the integrator in a way tending to reduce the error. The circuit is designed and adjusted to be critically damped. Thus, if there is an error in the output due to the integrator being a little in error it will be corrected to a high degree in the next sample period. If, for example, the integrator is accurate to within 1% and if there is a step change of one volt and leading to a 1.01 volt measured value due to the 1% error of the integrator and if there is a continuing constant input, the next measured value will show that error is reduced by a factor of 100 in the next sample. The circuit is thus self-correcting and the static gain through the circuit can be shown to be dependent on matched resistor values rather than on the value of C11 in the integrators.

It will be found that during the 16.7 milliseconds S2 (S4) is closed and S1 (S3) is open the last sample is compared with whatever appears on the new sample; there may be ringing on the waveform, the waveform may have 60 cycle noise, the waveform may be increasing or decreasing, but whatever is going on in that waveform, each point will be equally weighted. This error integration makes the new output an integrated average of the signal levels which occurred during the 16.7 millisecond pulses. S1 (S3) and S2 (S4) are complementary switches. At the end of the S2 closure (S1 being open), S2 opens and S1 closes; the integrator now has no input and becomes the holding circuit whereas during the preceding period of the cycle the sampling circuit is following the input through switch S2. This just rises to the value of the integrator of S1 (S3).

The correction for the pneumotach characteristics is developed by forming the inverse of the function ($k_1 F + k_2 F^{k_3}$). These manipulations are performed in a nonlinear compensating circuit identified at 130 and the basic method used is use of electronic logarithm and antilog circuits. Thus, the barometric pressure (for $k_2$) is entered into a microprocessor (not shown) and the reciprocal of its value is applied to a sample hold circuit at Q1 that is strobed by the P-strobe input which also comes from the microprocessor. The analogue circuitry includes a sample hold circuit consisting of amplifier Z12 and associated components that have a current-voltage level which is proportional to one over the barometric pressure. This level is subsequently applied to the log circuit that consists of operational amplifier 132 and a transistor in circuit Z6 to form the quantity log 1/B. This location is marked in the circuitry. Coming back to the output of amplifier Z3A this output passes through an absolute value circuit consisting of operational amplifiers Z3C and Z7A having individual scaling controls for the positive and negative components in order to make linearity adjustments. The absolute value output from the absolute value circuit is applied to the log circuit consisting of Z7 and a transistor in the integrating circuit Z6 and the location of the resulting log function designated log absolute value of F (log $|F|$) which is the output of this log circuit is marked on the schematic. These two quantities log 1/B and log $|F|$ are then summed and amplified by the circuit including operational amplifier Z7A in such a way as to produce the quantity log $k_3|F| + \log B$. This quantity now is supplied to a pair of transistors in circuit Z6 so as to provide in two places the antilog quantity output $B|F|^{k_3}$. It should be understood that certain scaling factors may apply so that these values are proportional values. One antilog output is applied directly to the inverting input of operational amplifier Z3A and provides the feedback required to get the correction for one polarity. Since, however, the absolute value of the flow was taken, positive feedback to operational amplifier Z3A would not produce the correction needed, i.e., a change of sign may be needed. This is accomplished by applying the other antilog output to the circuit consisting of four transistors designated Z in such a way that the quantity $-2B|F|^{k_3}$ is produced. This output is mixed with the original antilog $B|F|^{k_3}$ so as to provide the quantity $-B|F|^{k_3}$ which is the actual, mixed signal applied to the inverting input of operational amplifier Z3A when needed as controlled by comparator Z3C whose output is dependent on the sign of the output of amplifier Z3A.

Describing the function of operational amplifier Z3B in scale factor adjusting circuit 56, the function of this amplifier and associated circuitry is to provide a means of adjusting the scale factor of one direction of flow relative to the scale factor existing in the other direction in order to compensate for imbalances in the pneumotach head or other imbalances that may occur. The flow signal is rectified so that only the negative portion of the signal is passed by amplifier Z3B and this output is applied to both the inverting and non-inverting inputs of amplifier Z3A in a proportion that is adjustable by the potentiometer control labelled BAL (for balance) and this is used in the calibration of this instrument.

FIGS. 7A–7L illustrate the waveforms as they appear in selected portions of the electronic circuitry just described. The locations where the signals of FIGS. 7C through 7L have been taken are labelled on the drawing.

Operation of the gas flow measuring system of the present invention can now be summarized. When flow is present in the pneumotach head the pressure difference across the flow restriction is transmitted via flexible gas tubes to the smoothing chambers of the chopper assembly. These chambers are connected to respective piezoelectric transducer chambers through the rotary valves in the chopper which reverses the pneumatic connections to the pressure transducer 40 times per second. In this manner the pressure transducer output is converted to a 20 hertz AC signal. The vane which is attached to the rotary valve passes through a pair of photosensors as described which provide positive valve positioning information. The AC amplifier is used to amplify the transducer signal and the output is inverted in one of two processing channels providing a pair of sampling circuits. These sampling circuits are each supplied thus at a 20 hertz rate with a series of 16.7 millisecond pulses which interleave so that a 40 samples per second sampling rate is obtained. The valve position information derived from the photosensors circuits is incorporated into a set of timing circuits to generate sampling pulses coinciding with the tops and bottoms of the transducer output. The sampling circuits also serve to integrate the sum of two successive sampled signals. The dimension of the integrator is such that for a constant input the difference disappears during the 16.7 millisecond sampling period. Any residual error appears as its square in the next sample. For example, an error of 1% is effectively reduced to 0.001% in the next sample. The 16.7 millisecond sampling period is chosen to achieve line synchronous noise immunity so that both the line synchronous noise and DC drift are eliminated. The outputs of the sampling circuits are summed and since the amplitude output of one amplifier is inverted, the sum of any DC component in the output thereof is zeroed.

What is claimed is:

1. In a gas flow measuring system, a pneumotach including means forming a flow channel, means forming a flow restriction in said channel defining on opposite sides thereof first and second portions A, B, a pressure transducer having first and second opposite sides $\alpha$, $\beta$, said pressure transducer being constructed and arranged to deliver an electric signal in response to pressure differential applied thereto, pneumatic switch means for connecting said pressure transducer to said flow channel in the sequence A to $\alpha$, B to $\beta$; A to $\beta$, B to $\alpha$; A to $\alpha$, B to $\beta$; ... so that said pressure transducer is alternately connected to opposite sides of said restriction, means enclosing said pressure transducer and pneumatic switch means in a sealed chamber solely connected to said pneumotach, means connected to the output of said pressure transducer for developing an electric flow signal in correspondence with the pressure difference applied thereto, means for enclosing the transducer within an enclosed volume including means forming matched chambers A, B, having equal volume on each side of said transducer, means for sampling over a predetermined substantial interval during each alternate connection of said transducer to the electric signal developed thereby and for integrating the valve thereof to develop signals $a_n$, $b_n$, means for developing a flow signal from said signals $(a_n - b_m)$.

2. A system as in claim 1 further including means for forming the progressive series $(a_n - b_n)$, $(a_n - b_{n+1})$, $(a_{n+1} - b_{n+1})$ as approximate $\Delta P$ values.

3. A system as in claim 2 further including means for generating the inverse function of $\Delta P = k_1(F + k_2 F^{k3})$ for F where F is flow and for applying the same to the summed difference in pressure signal from said system to develop a signal proportional to flow in said channel.

4. In a gas flow measuring system having a pneumotach for receiving a flowing gas and including a flow restriction having sides A and B thereacross, a pressure transducer for producing a signal from which the gas flow is measured when connected across said flow restriction and having opposite side chambers $\alpha$, $\beta$, and chopper means connected between said flow restriction and said transducer for alternating connections between said opposite side chambers $\alpha$, $\beta$ of said pressure transducer and the sides A, B of said flow restriction, the improvement comprising: means forming separate channels and pressure smoothing chambers of equal volumes for respectively connecting said pressure transducer side chambers to said flow restriction sides in said alternating sequence.

5. A gas flow measuring system as in claim 4 further including an amplifier for said transducer signal including first and second electronic signal processing channels, said first channel including a unity gain inverting amplifier, each channel having an input sample switch and an output hold switch, and means for developing control pulses for opening and closing said switches from the state of said chopper means connection between said sides of said flow restriction and said chambers of said pressure transducer.

6. In a gas flow measuring system in which the pressures on opposite sides of a pneumotach restriction from gas flow therein are sampled with a gas chopper connected to a pressure detecting transducer, the method of causing the gas chopper to alternate the pressures backward and forward in application to the transducer so that the latter develops an AC signal the strength of which is related to the pressures, sampling this AC signal is synchronism to the alternate pressure application of the gas chopper over intervals having a duration related to the power line frequency and integrating the same to develop integrated values of the sampled signals free of drift caused by power line interference, summing the integrated values at double the gas chopper pressure alternating rate to give a smooth output, and manipulating the latter in a linearizing circuit to obtain a flow signal which is proportional to the flow.

7. In a gas flow measuring system in which the pressures on opposite sides of a pneumotach restriction from gas flow therein are sampled with a gas chopper connected to a pressure detecting transducer, the improvement comprising: means for causing the gas chopper to alternate the pressures backward and forward in application to the transducer so that the latter develops an AC signal the strength of which is related to the pressures, means for sampling this AC signal is synchronism to the alternate pressure application of the gas chopper over intervals having a duration related to the power line frequency and integrating the same to develop integrated values of the sampled signals free of drift caused by power line interference, means for summing the integrated values at double the gas chopper pressure alternating rate to give a smooth output, and means for manipulating the latter including a linearizing circuit to obtain a flow signal which is proportional to the flow.

8. A gas flow measuring system as in claim 7 wherein the means for sampling further comprise hold means for deriving separate successive signals $a_1$, $a_2$, $a_3$, $a_4$ ... and $b_1$, $b_2$, $b_3$, $b_4$ ... and, in combination with the means for summing, for developing the signals of the type $(a_n - b_m)$.

9. A gas flow measuring system as in claim 7, wherein said means for manipulating comprise means for developing said flow signal according to the relation $$\Delta P = k_1(F + k_2 F^{k3})$$

where $\Delta P$ is the processed pressure transducer signals $a_n - b_m$, $k_1$ and $k_3$ are empirically determined constants, $k_2$ is a scaled value of the barometric pressure, and F is the flow signal representing the gas flow through said channel.

10. A system as in claim 7 wherein the sampling means form the signals $(a_n - b_m)$ as the progressive series $(a_n - b_n)$, $(a_n - b_{n+1})$, $(a_{n+1} - b_{n+1})$ as approximate $\Delta P$ values.

11. A system as in claim 10 wherein the means for manipulating generate the inverse function of $\Delta P = k(F + k_2 F^{k3})$ for F where F is the flow and $k_1$, $k_3$ are empirically determined constants, and $k_2$ is a constant proportional to the barometric pressure.

* * * * *